United States Patent [19]
Pegg et al.

[11] Patent Number: 5,279,955
[45] Date of Patent: Jan. 18, 1994

[54] HETEROFUNCTIONAL CROSSLINKING AGENT FOR IMMOBILIZING REAGENTS ON PLASTIC SUBSTRATES

[76] Inventors: Randall K. Pegg, 5085 First Coast Hwy., Amelia Island, Fla. 32034; Mary S. Saunders, Rte. 3 Box 106-1, Monticello, Fla. 32344

[21] Appl. No.: 663,120

[22] Filed: Mar. 1, 1991

[51] Int. Cl.$^5$ ............... C12N 11/06; G01N 33/549; C07C 69/34
[52] U.S. Cl. .................... 435/181; 435/7.92; 436/532; 530/816; 560/190
[58] Field of Search ............ 435/181, 7.92; 434/532; 530/816; 560/190

[56] References Cited
U.S. PATENT DOCUMENTS

| | | | |
|---|---|---|---|
| 4,229,537 | 10/1980 | Hodgins et al. | 435/181 X |
| 4,657,873 | 6/1987 | Gadow et al. | 436/532 |
| 4,808,530 | 2/1989 | Means et al. | 435/180 |
| 4,889,916 | 12/1989 | Packard et al. | 435/181 X |
| 5,002,883 | 3/1991 | Bieniarz et al. | 435/181 X |

FOREIGN PATENT DOCUMENTS 2184127 6/1987 United Kingdom.

*Primary Examiner*—David M. Naff
*Attorney, Agent, or Firm*—R. Kevin Pegg

[57] ABSTRACT

Heterofunctional crosslinking agents are synthesized that covalently link molecules such as enzymes, cells, proteins and nucleic acids to a plastic substrate. The agents contain a central ring structure having a hydrophobic hydrocarbon chain that binds to a plastic substrate and distal to the hydrophobic chain one or more hydrophilic chains terminating in a reactive group that covalently binds the molecule. Immobilized molecules are useful in diagnostic assays or bioreactors. A preferred heterofunctional crosslinking agent is succinyl-olivetol-N-hydroxysuccinimide having the structure:

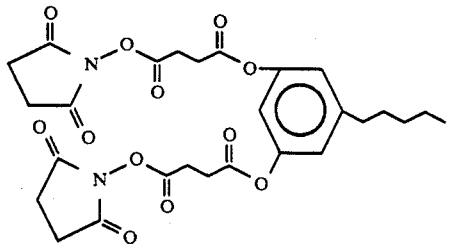

This agent is prepared by reacting succinic anhydride with 5-pentyl resorcinol and condensing carboxylic acid groups with N-hydroxysuccinimide.

4 Claims, 2 Drawing Sheets

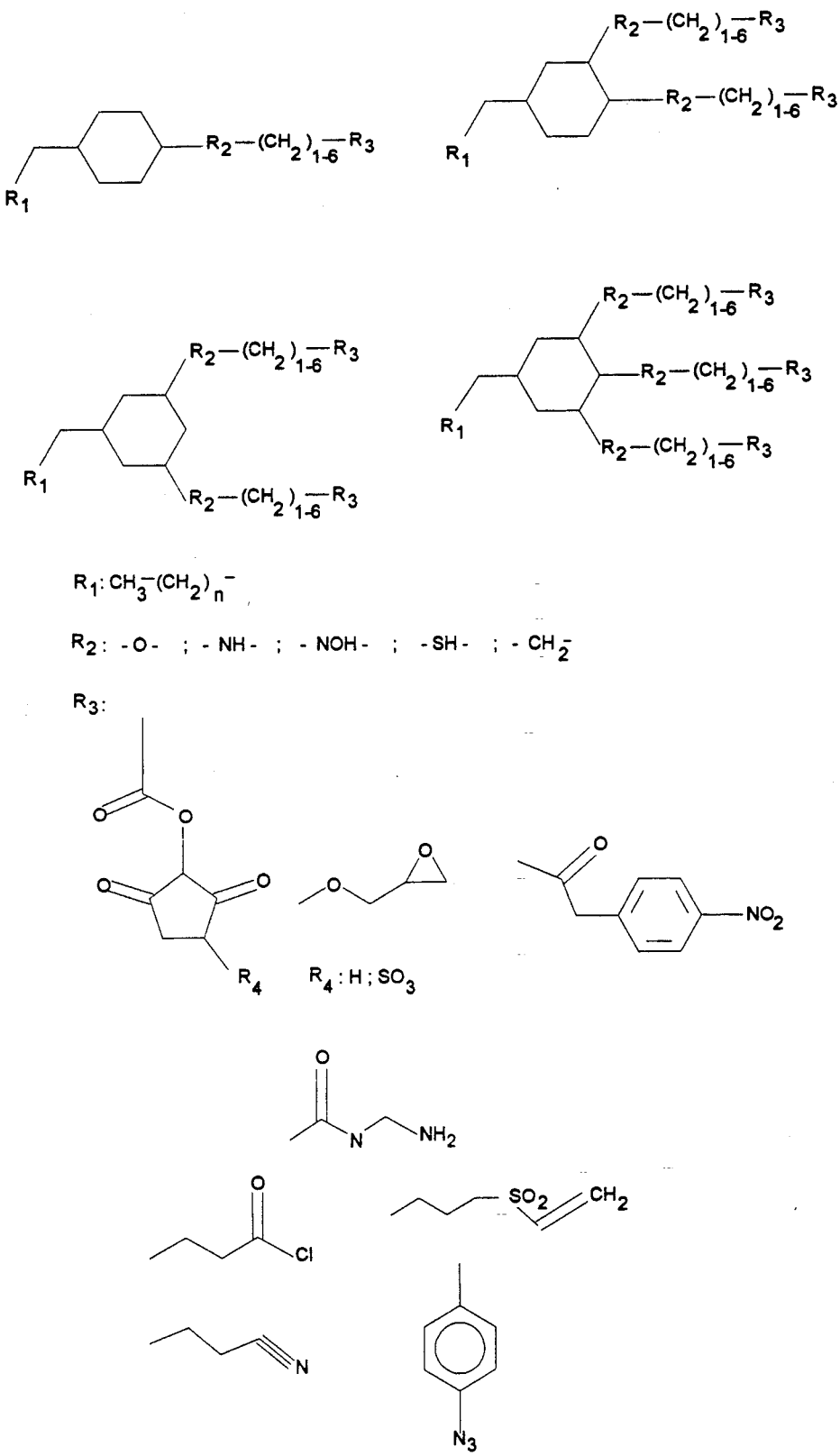
Fig. 1: Side groups used to form heterofunctional molecules.

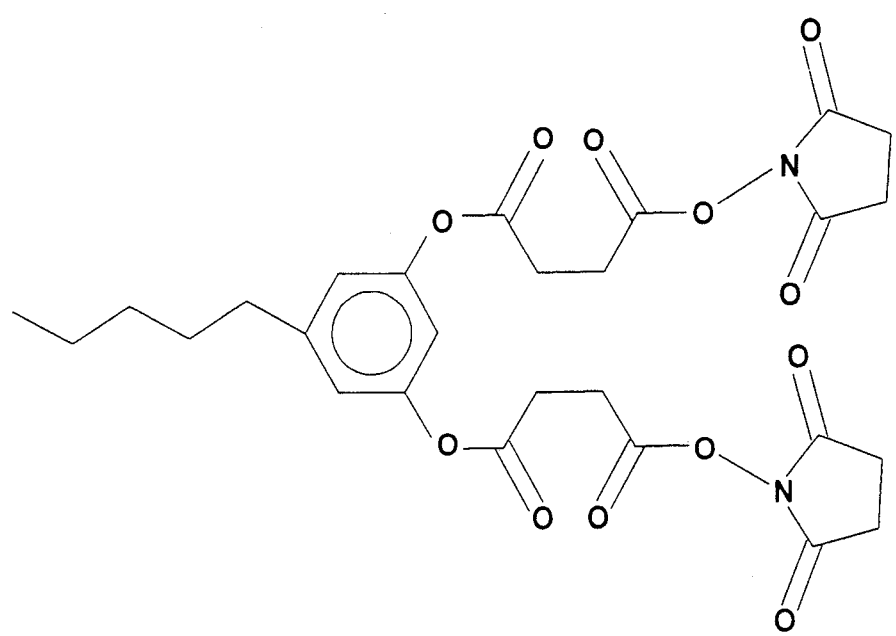
Fig. 2: Heterofunctional molecule as described in Example 1.

HETEROFUNCTIONAL CROSSLINKING AGENT FOR IMMOBILIZING REAGENTS ON PLASTIC SUBSTRATES

BACKGROUND OF THE INVENTION

1. Field of the Invention

This invention relates to a novel heterofunctional composition useful in immobilizing reagents on plastic surfaces. More specifically this invention comprises a molecule with hydrophobic regions that can intercalate into plastic and a hydrophilic reactive group that can covalently attach to other molecules.

2. Background Information

The practice of biotechnology, and particularly diagnostics, has increased the demand for products requiring immobilized reagents. "Reagents" includes proteins, nucleic acids, cells, drugs, and small molecule haptens. Substrates are insoluble matrices for immobilization and can be plastic, glass, silica, carbon, cellulose, or other materials. Plastics are particularly useful substrates as they can be formed into a variety of shapes, such as cups, discs, "dipsticks", spheres, tubes, membranes, and particles. Additionally, plastics have a high degree of biocompatability, and may be produced of materials having excellent optical properties. Typical plastics useful as substrates include polypropylene, polystyrene, polyethylene, polyvinyl chloride, polysulfone, polycarbonate, cellulose acetate, and others. Polystyrene, polyvinyl chloride, and polycarbonate are widely used substrates when optical properties are a consideration. Plastics themselves are often used as substrates for direct immobilization of macromolecules. Polystyrene and polyvinyl chloride will anchor large molecules by electrostatic attraction. However, small molecules require attachment to larger "carrier" molecules to be bound. Also, poor absorption to most plastics limit the use of absorption immobilization to high surface area systems. For instance, polystyrene latex particles can immobilize protein molecules although molded polystyrene products usually require plastic modifying agents due to the limited surface area.

Modification of the plastic surface has been used to increase the electrostatic interaction and increase the binding of some reagents. Electrostatic interactions alone will immobilize only a limited number of reagents, and when detergents are introduced in the system reagent loss can occur.

Reagent molecules are typically immobilized on a substrate by way of a linker molecule. Homofunctional and heterofunctional compounds have been devised to link a group present on the reagent to a group present on the substrate. As an example, disuccimidyl suberate is a homofunctional compound that can covalently bridge an amine group on a reagent molecule to an amine group present on a substrate, such as aminopolystyrene. Additionally, some plastics, such as methyl methacrylate and polyethylvinylacetate, have been developed to bear hydroxyls that can be converted to reactive intermediates. Reactive groups that can be provided include epoxides, hydroxy succinimide esters, aldehydes, nitrophenyl chloroformate, activated thiols, trityl, tresyl chloride, or other means for reacting free amines, hydroxides or sulfhydryls.

Modification of the plastic surfaces to bear amines, hydroxyls, and sulfhydryls that can be crosslinked or otherwise modified has resulted in undesirable characteristics, particularly opacity.

One system that has become available involves incorporation of a methyl imine function. This product requires the end user to convert the methyl imine functionality to a reactive group by addition of crosslinkers (NUNC, Naperville, Ill.). Another system treats plastic with a copolymer of phenylalanine and lysine amino acids to provide a support for a crosslinker (U.S. Pat. No. 4,657,873; Gadaro, 1987).

Thus, a need continues to exist for a heterofunctional product that can directly modify a plastic surface to provide a covalent coupling means.

SUMMARY OF THE INVENTION

The invention comprises a heterofunctional molecule and plastic substrate to covalently immobilize a reagent. Substrates are articles of plastic and may be formed into beads, rods, cups, membranes, or tubes. Substrates may be of polymers of vinyl, ethylene, propylene, sulfone, carbonate, or a combination thereof. The heterofunctional molecule comprises a molecule having three distinct regions. More specifically the molecule has a central ring structure and two functional groups at opposite positions. One functional region is a hydrocarbon "tail" or chain of three or more ethyl groups terminating in a methyl function. A second region joins at the ring position distal to the hydrocarbon tail and comprises one or more hydrophilic chains terminating in a reactive functional moiety. The reactive groups join the central ring at points which are hydrophilic in nature. This feature aids in the orientation of this molecule, highly hydrophobic on one end, wettable on the opposite end.

Reactive groups are those molecules that can react with a group on the reagent member for immobilization. Reactive groups include, but are not limited to, hydroxy succinimide, nitrophenyl chloroformate, activated thiol, trityl, tresyl chloride, acid halides, epoxides, diazo, or any other reactive group.

An important feature is the diverse types of assays that can be performed using this invention including, but not limited to, immunoassay for diagnosis involving colorimetric, fluorometric and radiometric means, affinity assays, chromatography, ligand mediated analysis, and facilitated cell adhesion studies. The invention could be used to produce immobilized cell and enzyme bioreactors or as a novel adhesive and surface modifying agent.

BRIEF DESCRIPTION OF THE DRAWINGS

FIG. 1 depicts the design of the heterofunctional agent. R1 illustrates the hydrocarbon tail. R2 illustrates the hydrophilic appendages bridging the reactive groups with the hydrophobic regions. R3 demonstrates some of the types of reactive groups that can be substituted.

FIG. 2 shows the heterofunctional crosslinker developed using 5 pentyl resorcinol as a starting material.

DETAILED DESCRIPTION OF THE INVENTION

The invention for immobilizing reagents comprises, a substrate; a heterofunctional molecule having a hydrophobic tail attached to a central ring, and in a separate structure on the ring opposite from the hydrophobic tail a hydrophilic region with a reactive group; and a reagent molecule capable of covalently attaching to the reactive group.

In a preferred embodiment the hydrophobic tail comprises a chain extending from the central ring further comprising at least two ethyl groups terminating in a methyl group; the hydrophobic tail capable of intercalating the plastic substrate thereby anchoring the molecule and orienting the reactive moieties. In a preferred embodiment a second functional region comprises one or more hydrophilic chains terminating in a reactive functional moiety joined at the ring position distal to the hydrocarbon tail. In a further embodiment the point at which the reactive groups are bound to the ring is a hydrophilic bond such as an amine, hydroxyl, imine, hydroxylamine, carboxylic acid or other. It is an embodiment of this invention that when an aqueous solution of the reagent is applied the association of the hydrophobic region with the substrate is essentially irreversible and reactive groups extend into the solution to react with the reagent molecules.

In a particularly preferred embodiment the heterofunctional molecule is derived from reacting succinic anhydride to 5-pentyl resorcinol. The carboxylic acid groups thus obtained are then condensed with N-hydroxy succinimide to produce reactive esters. The types of molecules that can be immobilized to the plastic by this molecule include, but are not limited to, enzymes, antibodies- either monoclonal or polyclonal, cellular proteins, nucleic acids including DNA, RNA and oligonucleotides, drugs, and xenobiotics.

Preferred substrates are plastics derived from polymers of vinyl, ethylene, propylene, sulfone, carbonate, or a combination thereof. In a preferred embodiment the plastic substrate is a molded article, a pellicular or porous bead, or a porous sheet such as a membrane. In a particularly preferred embodiment the substrate is polystyrene formed in the shape of a microtiter plate well.

Reagents comprise protein, nucleic acid, hapten or cell materials. Proteins are the preferred embodiment, in a particularly preferred embodiment the immobilized protein is an antibody directed against an analyte to be measured in an assay. "Assays" in these embodiments comprise analysis of drugs, haptens, proteins, nucleic acids, cells, or other molecules relevant to diagnosis. A full description of immunoassay methods are described in Tijssen, PRACTICE AND THEORY OF ENZYME IMMUNOASSAYS, LABORATORY TECHNIQUES IN BIOCHEMISTRY AND MOLECULAR BIOLOGY (1985) herein incorporated by reference.

This disclosure will enable those skilled in the art to grasp the potential of this novel heterofunctional agent to produce a variety of immobilized products. Examples herein described are meant to be illustrative only and not limitive on the scope of the invention.

The following reagents were used in the course of developing this invention. Sources are given where relevant, otherwise they are of the standard commercial grades available.

Phosphate buffered saline (PBS): 0.1M, pH 7.2. Available from Sigma Chemical, St. Louis Mo.

PBS-Tween: PBS solution above with 0.1% Tween detergent.

Carbonate buffer:

0.05M Solution. Available from Sigma Chemical, St. Louis Mo.

Non-specific blocking solution (NSB solution): Bovine serum albumin (Intergen, Purchase N.Y.), 1 g, with 0.5 g trehalose added to 200 mls phosphate buffer.

Enzyme conjugate solution:

Goat anti-rabbit IgG conjugated to horseradish peroxide, available from Sigma Chemical, St. Louis Mo., was diluted in NSB solution.

Enzyme substrate:

Tetramethyl benzidine solution was obtained from Kirkegaard and Perry, Gaithersberg Md.

EXAMPLE 1

Synthesis of succinyl-olivetol-N-hydroxy succinimide (SON) compound shown in FIG. 2 was accomplished as follows. All materials and solvents were obtained from Aldrich Chemicals (Milwaukee, Wis.. 0.1 gram of pentyl resorcinol wa dissolved in 2 mls dioxane. In a separate container anhydrous N-hydroxysuccinimide equivalent to in excess of two moles w/w was dissolved in two mls dioxane. Both solutions were mixed into a sealed glass vessel under nitrogen and sonicated for 60 minutes in a 45 watt sonicating bath, followed by 6 hours at 60 degrees C. The solvent was removed under a nitrogen stream and the brown oil thus obtained was resuspended in dichloromethane. The solution was washed with two volumes of water, and the organic phase was dried with molecular sieve and the solvent removed under a nitrogen stream. The oil was resuspended in dioxane and N-hydroxysuccinimide equivalent to two moles w/w were added. The final compound was obtained by adding the condensing agent dicyclocarbodiimide.

The crystals of dicyclourea were removed by filtration and the resulting SON purified by standard chromatographic means. The usefulness of this compound is demonstrated by the following example.

Comparison of antibody binding on Immulon I coated with SON.

Immulon I microtiter plates (Dynatech) were coated with SON diluted 1/150 in methanol or were uncoated blanks. Rabbit anti-sulfamethazine antibody diluted 1/200 in carbonate buffer was added to each well and incubated one hour at room temperature. Wells were washed three times with PBS -tween and non specific reactions blocked with BSA-Trehalose. Anti rabbit enzyme conjugate was added to each well and incubated one half hour at room temperature. Wells were washed three times with PBS -tween and TMB substrate added to each well. SON greatly increased the binding of anti-sulfamethazine on Immulon I plates (Table 1).

TABLE 1

| ELISA Comparisons of antibody attachment with and without SON. | | |
|---|---|---|
| Plate Type | SON | BLANK |
| Immulon I | 0.534 | 0.169 |
| | 0.513 | 0.166 |
| | 0.586 | 0.167 |

EXAMPLE 2

Succinyl-olivetol-N-hydroxysuccinimide prepared as described above is used to produce plastic articles other than microtiter plates. SON dissolved to a concentration of 2 mg/ml in methanol and added to 0.1 gram of polyethylvinyl acetate beads, 10 microns average diameter (Polysciences, Warrington, Pa.). After evaporation of the solvent under a nitrogen stream the beads are capable of immobilizing protein reagents.

EXAMPLE 3

Using pentyl resorcinol as a starting material a second derivative is made. Pentyl resorcinol is dissolved in dioxane. Two moles of glutaric anhydride are added and reacted at temperatures and conditions sufficient to produce the ester. The free carboxyllic acid groups on glutarate are converted to the corresponding acid chlorides through the action of thionyl chloride. The reagent thus obtained have the ability to crosslink amines, imines, and hydroxylated compounds to plastic surfaces under both aqueous and organic conditions.

What is claimed is:

1. A heterofunctional crosslinking agent for immobilizing a reagent on a plastic substrate, said agent comprising:

the molecule, succinyl-olivetol-N-hydroxysuccinimide, of the structure:

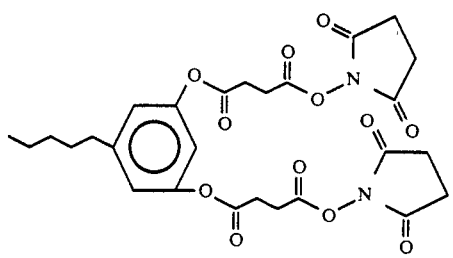

wherein said

of the structure is a hydrophobic member for bonding said molecule to a plastic substrate, and said

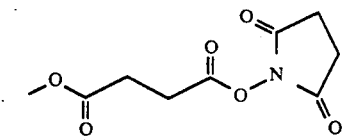

of the structure are hydrophilic members having a terminal reactive group for binding a reagent.

2. The heterofunctional crosslinking agent of claim 1 wherein said agent is bound by said hydrophobic member to a plastic substrate made from a polymer selected from the group consisting of polypropylene, polyethylene, polycarbonate, polysulfone, polyvinyl, polymethacrylate, and derivatives and combinations thereof; said plastic being in the form of a sheet, cup, rod, tube, or bead, either porous or non-porous.

3. The heterofunctional crosslinking agent of claim 2 wherein a reagent is bound to said hydrophilic members and said reagent is selected from the group consisting of an enzyme; antibody, either monoclonal or polyclonal; amino acid; cell, either microbial, plant, or animal; wherein said reagent is useful in diagnostic assays or bioreactors.

4. The heterofunctional crosslinking agent of claim 2 wherein a drug or drug analog useful in diagnostic assays is bound to said hydrophilic members.

* * * * *